(12) United States Patent
Dwivedi et al.

(10) Patent No.: US 9,409,912 B2
(45) Date of Patent: Aug. 9, 2016

(54) PROCESS FOR THE PREPARATION OF SITAGLIPTIN PHOSPHATE

(71) Applicant: CADILA HEALTHCARE LIMITED, Ahmedabad, Gujarat (IN)

(72) Inventors: Shri prakash Dhar Dwivedi, Gujarat (IN); Kumar Kamlesh Singh, Gujarat (IN); Sunil Dnyaneshwar Narode, Gujarat (IN); Dhaval Jashvantbhai Patel, Gujarat (IN); Kirtipalsinh Sajjansinh Solanki, Gujarat (IN)

(73) Assignee: CADILA HEALTHCARE LIMITED, Ahmedabad (IN)

( * ) Notice: Subject to any disclaimer, the term of this patent is extended or adjusted under 35 U.S.C. 154(b) by 0 days.

(21) Appl. No.: 14/220,836

(22) Filed: Mar. 20, 2014

(65) Prior Publication Data
US 2015/0087834 A1    Mar. 26, 2015

(30) Foreign Application Priority Data
Mar. 20, 2013    (IN) .......................... 916/MUM/2013

(51) Int. Cl.
    *C07D 487/04*    (2006.01)
(52) U.S. Cl.
    CPC .................... *C07D 487/04* (2013.01)
(58) Field of Classification Search
    USPC ........................................................ 544/350
    See application file for complete search history.

(56) References Cited

U.S. PATENT DOCUMENTS
6,699,871 B2    3/2004    Edmondson et al.
(Continued)

FOREIGN PATENT DOCUMENTS
WO    2010/122578        10/2010
WO    2012/150328 A1    11/2012
WO    2013/013833 A1    1/2013

OTHER PUBLICATIONS
Han et al Tetra. vol. 60 pp. 2447-2467 (2004).*
(Continued)

*Primary Examiner* — Noble Jarrell
(74) *Attorney, Agent, or Firm* — Ladas & Parry LLP

(57) ABSTRACT

The present invention relates to a method for the preparation of sitagliptin phosphate and sitagliptin phosphate anhydrous of Formula (I') and monohydrate of Formula (I),

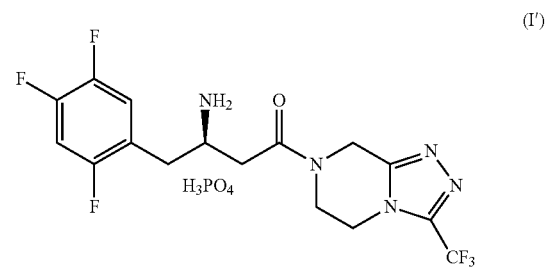

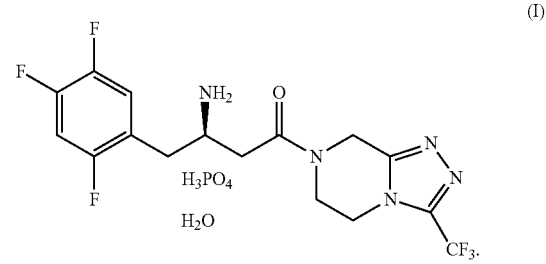

17 Claims, 5 Drawing Sheets

(56) References Cited

U.S. PATENT DOCUMENTS

| | | | |
|---|---|---|---|
| 7,326,708 B2 | 2/2008 | Cypes et al. | |
| 7,495,123 B2 | 2/2009 | Xiao et al. | |
| 8,309,724 B2 * | 11/2012 | Padi et al. | 544/350 |
| 8,334,385 B2 * | 12/2012 | Arjunan et al. | 544/350 |
| 8,389,724 B2 * | 3/2013 | Winter et al. | 544/350 |
| 8,624,026 B2 * | 1/2014 | Kim et al. | 544/350 |
| 8,846,916 B2 * | 9/2014 | Gore et al. | 544/350 |
| 8,912,327 B2 * | 12/2014 | Rasparini et al. | 544/350 |
| 2009/0123983 A1 | 5/2009 | Niddam-Hildesheim | |
| 2009/0192326 A1 | 7/2009 | Perlman et al. | |

OTHER PUBLICATIONS

AAPPTEC, Coupling Reagents (2001).*

Kim, D., et al., "(2R)-4-oxo-4[3-(trifluoromethyl)-5,6-dihydro[1,2,4]triazolo[4,3-a]pyrazin-7(8H)-yl]-1-(2,4,5-trifluorophenyl) butan-2-amine: a potent, orally active dipeptidyl peptidase IV inhibitor for the treatment of type 2 diabetes", J. Med Chem Jan. 13, 2005;48(1): 141-51, abstract.

* cited by examiner

PROCESS FOR THE PREPARATION OF SITAGLIPTIN PHOSPHATE

FIELD OF THE INVENTION

The field of present invention relates to an improved process for the preparation of sitagliptin phosphate. More particularly, the invention relates to an improved process for preparation of sitagliptin phosphate anhydrous of Formula (I') or monohydrate of Formula (I).

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Sitagliptin (CAS 486460-32-6) is an oral antihyperglycemic (antidiabetic) drug of the dipeptidyl peptidase-4 (DPP-4) inhibitor class. It was developed, and is marketed, by Merck & Co under the trade name of JANUVIA. The tablets contain sitagliptin phosphate, an orally-active inhibitor of the dipeptidyl peptidase-4 (DPP-4) enzyme. This enzyme-inhibiting drug is used either alone or in combination with other oral antihyperglycemic agents (such as metformin or a thiazolidinedione) for treatment of diabetes mellitus type 2.

Sitagliptin phosphate monohydrate is chemically named as 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine phosphate (1:1) monohydrate and has the following structural Formula (I).

(I)

U.S. Pat. No. 6,699,871 B2 (the U.S. '871 patent) and *J. Med. Chem.* 2005, Vol. 48 (1), 141-151 discloses process for preparation of sitagliptin by coupling (3R)—N-(tert-butoxycarbonyl)-3-amino-4-(2,4,5-trifluorophenyl)butanoic acid of Formula (V) with 3-(trifluoromethyl)-5,6,7,8-tetrahydro-1,2,4-triazolo-[4,3-a]pyrazine of Formula (IV) or salt thereof under standard peptide coupling conditions by using 1-ethyl-3-(3-dimethylaminopropyl)carbodimide (EDC), 1-hydroxybenzotriazole (HOBT) and a base diisopropylethylamine in solvents like N,N-dimethylformamide (DMF) or methylene dichloride (MDC).

U.S. Pat. No. 7,326,708 B2 (the U.S. '708 patent) discloses preparation of sitagliptin dihydrogenphosphate salt and crystalline hydrates thereof, in particular a crystalline monohydrate and their pharmaceutical compositions. In particular, the U.S. '708 patent discloses preparation of sitagliptin phosphate salt by using one equivalent of phosphoric acid with respect to sitagliptin from 25° C. to 100° C. in organic solvent or aqueous organic solvent.

U.S. Pat. No. 7,495,123 B2 (the U.S. '123 patent) discloses process for preparation of enantiomerically enriched beta amino acid derivatives i.e. sitagliptin wherein the amino group is unprotected by asymmetric hydrogenation of a prochiral beta amino acrylic acid or derivative thereof, wherein the enamine amino group is unprotected, in the presence of a rhodium metal precursor complexed with a chiral mono- or bisphosphine ligand.

U.S. PG-Pub. No. 2009/0123983 A1 discloses the enzymatic reduction processes for the preparation of (S) or (R) methyl 4-(2,4,5-trifluorophenyl)-3-hydroxybutanoate, an intermediate in the synthesis of sitagliptin by combining methyl 4-(2,4,5-trifluorophenyl)-3-hydroxybutanoate with an enzyme that stereoselectively reduces a ketone to form an alcohol, and co-factor.

U.S. PG-Pub. No. 2009/0192326 A1 (the U.S. '326 A1) discloses a process for preparation of 3-amino-4-(2,4,5-trifluorophenyl)butanoic acid alkyl ester, an intermediate of sitagliptin and process for preparation of sitagliptin. The U.S. '326 A1 discloses reacting 3-tert-butoxycarbonylamino-4-(2,4,5-trifluorophenyl) butanoic acid with 3-(trifluoromethyl)-5,6,7,8-tetrahydro[1,2,4]triazolo[4,3-a]pyrazine hydrochloride in presence of dicyclohexylcarbodiimide as coupling agent and 4-dimethylaminopyridine (DMAP) as catalyst to obtain 4-(3-(trifluoromethyl)-5,6-dihydro-[1,2,4]triazolo[4,3-a]pyrazin-7(8H)-yl)-1-(2,4,5-trifluorophenyl)-4-oxobutan-2-yl-carbamate in N,N-dimethylformamide (DMF), and then removing the amino protected group in 4-(3-(trifluoromethyl)-5,6-dihydro-[1,2,4]triazolo[4,3-a]pyrazin-7(8H)-yl)-1-(2,4,5-trifluorophenyl)-4-oxo butan-2-yl-carbamate to obtain sitagliptin.

International (PCT) Publication WO 2010/122578 A2 discloses process for preparation of sitagliptin by coupling (3R)—N-(tert-butoxycarbonyl)-3-amino-4-(2,4,5-trifluorophenyl)butanoic acid of Formula (V) with 3-(trifluoromethyl)-5,6,7,8-tetrahydro-1,2,4-triazolo-[4,3-a]pyrazine hydrochloride of Formula (IV) under standard peptide coupling conditions using suitable condensing agent N,N'-Dicyclohexyl carbodiimide (DCC) in presence of hydroxybenzotriazole (HOBT) or 4-dimethylaminopyridine (DMAP).

International (PCT) Publication WO 2012/150328 A2 discloses alternative processes for the preparation of sitagliptin wherein N,N'-Dicyclohexyl carbodiimide (DCC) or 1-ethyl-3-(3-dimethyl-aminopropyl)carbodimide (EDC) is used as coupling agent in presence of hydroxybenzotriazole (HOBT).

International (PCT) Publication WO 2013/013833 A1 discloses the process for preparation of sitagliptin comprises reaction carried out under standard peptide coupling conditions, using 1-ethyl-3-(3-dimethylaminopropyl)carbodimide (EDC), 1-hydroxybenzotriazole (HOBT) and a base usually diisopropylethyl-amine, in a solvent such as N,N-Dimethylformamide (DMF) or methylene dichloride (MDC). The protecting group is then removed with trifluoroacetic acid or methanolic hydrogen chloride in the case of tert-butoxycarbonyl as protecting group.

Therefore, one of the objectives of the present invention is to provide an alternative approach for the preparation of sitagliptin which avoids use of standard coupling agents and which provides at least a useful alternative approach over the one disclosed in the art. In view of the above cited prior art, it is therefore, desirable to provide an efficient process for the preparation of sitagliptin.

SUMMARY OF THE INVENTION

In one general aspect, there is provided a process for the preparation of sitagliptin phosphate anhydrous of Formula (I') or monohydrate of Formula (I) comprising coupling (3R)—N-(tert-butoxycarbonyl)-3-amino-4-(2,4,5-trifluorophenyl)butanoic acid of Formula (V) with 3-(trifluoromethyl)-5,6,7,8-tetrahydro-1,2,4-triazolo-[4,3-a]pyrazine or its hydrochloride of Formula (IV), (V)

(IV)

(A)

in presence of O-(Benzotriazol-1-yl)-N,N,N',N'-tetramethyluronium tetrafluoroborate (TBTU) of Formula (A) as coupling agent.

In another general aspect, there is provided an improved process for the preparation of sitagliptin phosphate anhydrous of Formula (I') or monohydrate of Formula (I), (I')

(I)

the process comprising:
(a) coupling (3R)—N-(tert-butoxycarbonyl)-3-amino-4-(2,4,5-trifluorophenyl) butanoic acid of Formula (V),

(V)

with 3-(trifluoromethyl)-5,6,7,8-tetrahydro-1,2,4-triazolo-[4,3-a]pyrazine or its hydrochloride of Formula (IV),

(IV)

in presence of coupling agent TBTU and a base in first organic solvent to obtain (R)-tert-butyl 4-oxo-4-(3-(trifluoromethyl)-5,6-dihydro-[1,2,4]triazolo[4,3-a]pyrazin-7(8H)-yl)-1-(2,4,5-trifluorophenyl)butan-2-ylcarbamate of Formula (III);

(III)

(b) deprotecting the compound of Formula (III) with suitable acid in second organic solvent to obtain sitagliptin free base of Formula (II) by removal of organic solvent; and (II)

(c) treating the sitagliptin free base of Formula (II) with at least 1.4 mole equivalent of phosphoric acid in second organic solvent to obtain sitagliptin phosphate anhydrous of Formula (I'); or
(d) treating the sitagliptin free base of Formula (II) with at least 1.4 mole equivalent of phosphoric acid in second organic solvent optionally in presence of seed crystals to obtain sitagliptin phosphate monohydrate of Formula (I).

In another general aspect, there is provided an improved process for the preparation of (R)-tert-butyl 4-oxo-4-(3-(trifluoromethyl)-5,6-dihydro-[1,2,4]triazolo[4,3-a]pyrazin-7 (8H)-yl)-1-(2,4,5-trifluoro phenyl)butan-2-ylcarbamate of Formula (III), an intermediate for sitagliptin phosphate anhydrous of Formula (I') or its monohydrate of Formula (I), (III)

the process comprising coupling (3R)—N-(tert-butoxycarbonyl)-3-amino-4-(2,4,5-trifluorophenyl) butanoic acid of Formula (V) with 3-(trifluoromethyl)-5,6,7,8-tetrahydro-1,2,4-triazolo-[4,3-a]pyrazine or its hydrochloride of Formula (IV), (VI)

(V)

(IV)

in presence of coupling agent TBTU and a base in suitable organic solvent to obtain reaction mixture and obtaining compound OF Formula (III) by addition of water in the reaction mixture.

In another general aspect, there is provided sitagliptin phosphate anhydrous of Formula (I') or monohydrate of Formula (I) prepared by the process of present invention and having purity greater than 99.90%, or greater than 99.95% when measured by area percentage of HPLC.

In another general aspect, there is provided sitagliptin phosphate anhydrous of Formula (I') or monohydrate of Formula (I) substantially free from impurities, prepared by the process of present invention.

In another general aspect, there is provided a pharmaceutical composition comprising therapeutically effective amount of sitagliptin phosphate anhydrous of Formula (I') and one or more of pharmaceutically acceptable carriers, diluents or excipients.

In another general aspect, there is provided a pharmaceutical composition comprising therapeutically effective amount of sitagliptin phosphate monohydrate of Formula (I) and one or more of pharmaceutically acceptable carriers, diluents or excipients.

The details of one or more embodiments of the inventions are set forth in the description below. Other features, objects and advantages of the inventions will be apparent from the description.

DETAILED DESCRIPTION OF THE INVENTION

The inventors have discovered that use of O-(Benzotriazol-1-yl)-N,N,N',N'-tetramethyl-uronium tetrafluoroborate (TBTU) of Formula (A) as a coupling agent provides high purity intermediates, which in turn provides substantially pure sitagliptin phosphate anhydrous of Formula (I) or monohydrate of Formula (I').

All ranges recited herein include the endpoints, including those that recite a range "between" two values. Terms such as "about", "general", "substantially" and the like are to be construed as modifying a term or value such that it is not an absolute. This includes, at the very least, a degree of expected experimental error, technique error and instrument error for a given technique used to measure a value.

When a molecule or other material is identified herein as "substantially pure", it generally means, unless specified otherwise, that the material is about 99% pure or more. In general, this refers to purity with regard to unwanted residual solvents, reaction byproducts, impurities and unreacted starting materials.

As used here in the term "obtaining" may include filtration, filtration under vacuum, centrifugation, and decantation to isolate product. The product obtained may be further or additionally dried to achieve the desired moisture values. For example, the product may be dried in a hot air oven, tray drier, dried under vacuum and/or in a Fluid Bed Drier.

The terms used throughout the description is defined herein below.

"HOBT" refers to hydroxybenzotriazole.
"EDC" refers to 1-ethyl-3-(3-dimethylaminopropyl)carbodimide.
"DCC" refers to N,N'-Dicyclohexyl carbodiimide.
"TBTU" refers to O-(Benzotriazol-1-yl)-N,N,N',N'-tetramethyluronium tetrafluoroborate
"DMAP" refers to 4-dimethylaminopyridine.
"DMF" refers to N,N-dimethylforamide.
"DMAc" refers to N,N-dimethylacetamide.
"MDC" refers to methylene dichloride.
"DMSO" refers to N,N-dimethylsulfoxide.
"NMP" refers to N-methylpyrrolidone.
"THF" refers to tetrahydrofuran.
"IPA" refers to isopropanol.
"TEA" refers to triethylamine.
"TBA" refers to tert-butyl amine.
"DIPA" refers to diisopropyl amine.
"DIPEA" refers to diisopropyl ethylamine.
"DBU" refers to 1,8-diazabicyclo[5.4.0]undec-7-ene.

"DABCO" refers to 1,4-diazabicyclo[2.2.2]octane.
"DBN" refers to 1,5-Diazabicyclo[4.3.0]non-5-ene
"HPLC" refers to high performance liquid chromatography.

In one general aspect, there is provided an improved process for the preparation of sitagliptin phosphate anhydrous of Formula (I') or monohydrate of Formula (I) comprising coupling (3R)—N-(tert-butoxycarbonyl)-3-amino-4-(2,4,5-trifluorophenyl)butanoic acid of Formula (V) with 3-(trifluoromethyl)-5,6,7,8-tetrahydro-1,2,4-triazolo-[4,3-a]pyrazine or its hydrochloride of Formula (IV), (V)

(IV)

(A)

in presence of O-(Benzotriazol-1-yl)-N,N,N',N'-tetramethyluronium tetrafluoroborate (TBTU) of Formula (A) as coupling agent.

In another general aspect, there is provided an improved process for the preparation of sitagliptin phosphate anhydrous of Formula (I') or monohydrate of Formula (I), (I')

(I)

the process comprising:
(a) coupling (3R)—N-(tert-butoxycarbonyl)-3-amino-4-(2,4,5-trifluorophenyl) butanoic acid of Formula (V), (b)

(V)

with 3-(trifluoromethyl)-5,6,7,8-tetrahydro-1,2,4-triazolo-[4,3-a]pyrazine or its hydrochloride of Formula (IV), (IV)

in presence of coupling agent TBTU and a base in first organic solvent to obtain (R)-tert-butyl 4-oxo-4-(3-(trifluoromethyl)-5,6-dihydro-[1,2,4]triazolo [4,3-a]pyrazin-7(8H)-yl)-1-(2,4,5-trifluorophenyl)butan-2-ylcarbamate of Formula (III);

(III)

(e) deprotecting the compound of Formula (III) with suitable acid in second organic solvent to obtain sitagliptin free base of Formula (II) by removal of organic solvent; and (II)

(c) treating the sitagliptin free base of Formula (II) with at least 1.4 mole equivalent of phosphoric acid in second organic solvent to obtain sitagliptin phosphate anhydrous of Formula (I'); or (d) treating the sitagliptin free base of Formula (II) with at least 1.4 mole equivalent of phosphoric acid in second organic solvent optionally in presence of seed crystals to obtain sitagliptin phosphate monohydrate of Formula (I).

In general, the base comprises alkali metal hydroxides like sodium hydroxide, potassium hydroxide, lithium hydroxide; alkali metal carbonates like sodium carbonate, potassium carbonate and alkali metal bicarbonates like sodium bicarbonate, potassium bicarbonate; ammonia or its aqueous solution or organic bases like methyl amine, ethyl amine, TEA, TBA, DIPA, DIPEA, pyridine, piperidine, morpholine, DBU, DABCO or DBN and the like. In particular, DIPEA may be used.

In general, the first organic solvent comprises one or more of water, methanol, ethanol, isopropanol, ethyl acetate, isopropyl acetate, n-butyl acetate, acetone, methyl ethyl ketone, methyl isobutyl ketone, DMF, DMAc, DMSO, NMP, MDC, THF, 1,4-dioxane and the like. In particular, DMF or MDC may be used.

In general, the suitable acid comprises hydrochloric acid, triflouroacetic acid, sulfuric acid, pivalic acid, acetic acid, formic acid and the like. In particular hydrochloric acid or triflouroacetic acid may be used. The embodiments of the process comprises use of hydrochloric acid in form of its isopropanolic solution, hydrochloric acid gas or its solution in suitable solvent like acetone, ethyl acetate etc. More particularly, the isopropanolic hydrochloride solution may be used.

The second organic solvent comprises one or more of alcohols like methanol, ethanol, n-propanol, isopropanol, n-butanol; ketones like acetone, methyl ethyl ketone, methyl isobutyl ketone; chloro solvents like MDC, chloroform, ethylene dichloride and chlorobenzene; hydrocarbons like toluene, xylene, ethylbenzene; esters like ethyl acetate, isopropyl acetate, n-butyl acetate; ethers like tetrahydrofuran, diethyl ether, diisopropyl ether, methyl tert-butyl ether and polar solvents like water, DMF, DMAc, DMSO, NMP and the like. In particular, isopropanol may be used.

In general, the sitagliptin free base of Formula (II) may be obtained by the process comprising:

(a) removal of first organic solvent to obtain sitagliptin free base as semi-solid mass;

(b) treating the semi-solid mass with mixture of water immiscible solvent and water;

(c) treating the reaction mixture with base to adjust the alkaline pH;

(d) removing the separated aqueous layer and concentrating the organic layer to obtain semi-solid mass; and (e) treating the semi-solid mass with suitable organic solvent to obtain sitagliptin free base of Formula (II).

The first organic solvent may be removed by the known techniques in the art but not limited to distillation, distillation under vacuum, filtration, decantation, evaporation or evaporation under reduced pressure, centrifugation and the like. The removal of first organic solvent provides sitagliptin free base which may be isolated by usual work-up.

In general, the water immiscible solvent comprises one or more of methylene dichloride, toluene, xylene, ethyl acetate and the like. In particular, methylene dichloride may be used.

The base comprises of alkali metal hydroxides like sodium hydroxide, potassium hydroxide, lithium hydroxide; alkali metal carbonates like sodium carbonate, potassium carbonate and alkali metal bicarbonates like sodium bicarbonate, potassium bicarbonate; ammonia or its aqueous solution. In particular 40% sodium hydroxide solution may be used.

In general, the suitable organic solvent comprises one more of alcohols like methanol, ethanol, n-propanol, isopropanol, n-butanol; ketones like acetone, methyl ethyl ketone, methyl isobutyl ketone; hydrocarbons like toluene, xylene, ethylbenzene, hexane, heptane, cyclohexane; esters like ethyl acetate, isopropyl acetate, n-butyl acetate; ethers like tetrahydrofuran, diethyl ether, diisopropyl ether, methyl tert-butyl ether and the like or mixture thereof. In particular mixture of isopropanol and cyclohexane may be used.

In general, the embodiments of the process comprises treating the semi-solid mass of sitagliptin free base obtained by removal of isopropanol with mixture of methylene dichloride and water. The reaction mixture was treated with 40% sodium hydroxide to adjust the pH 12-13. The separated aqueous layer was extracted with methylene dichloride and combined organic layer was washed with water. The organic layer was distilled to remove methylene dichloride and co-distilled with cyclohexane. The semi-solid mass thus obtained was purified in mixture of isopropanol and cyclohexane at 50° C. to 80° C., in particular at 70° C. to 75° C. to obtain sitagliptin free base of Formula (II).

The embodiments of the process include treating sitagliptin free base of Formula (II) with at least about 1.4 equivalents of phosphoric acid in second organic solvent or mixture thereof with water. In particular, the sitagliptin free base may be treated with 85% phosphoric acid in mixture of isopropanol and water to obtain sitagliptin phosphate anhydrous of Formula (I).

The inventors of the present invention surprisingly found that, usage of less than 1.4 equivalent of 85% phosphoric acid as disclosed in prior arts herein above results in sitagliptin phosphate having low phosphate content by IC (Ion Chromatography).

TABLE 1

| Sr. No. | Sitagliptin Free Base gm | Sitagliptin Free Base mmol | Solvent: IPA ml | Solvent: IPA Vol | 85% $H_3PO_4$ gm | 85% $H_3PO_4$ mmol | Mole Equivlaent | Phosphate Content | Anhydrous/ Monohydrate* |
|---|---|---|---|---|---|---|---|---|---|
| 1 | 2.5 | 4.93 | 30 | 12 | 0.51 | 5.2 | 1.06 | 17.1 | Monohydrate |
| 2 | 2.5 | 4.93 | 12.5 | 5 | 0.61 | 6.24 | 1.27 | 15.69 | Monohydrate |
| 3 | 9 | 22.06 | 81 | 9 | 2.82 | 28.78 | 1.30 | 17 | Monohydrate |
| 4 | 9 | 22.06 | 81 | 9 | 2.82 | 28.78 | 1.30 | 16.81 | Monohydrate |
| 5 | 100 | 245.5 | 900 | 9 | 33.68 | 343.7 | 1.40 | 18.02 | Monohydrate |
| 6 | 100 | 245.5 | 900 | 9 | 33.68 | 343.7 | 1.40 | 18.28 | Monohydrate |
| 7 | 100 | 245.5 | 900 | 9 | 33.38 | 343.7 | 1.40 | 19.74 | Anhydrous |
| 8 | 100 | 245.5 | 900 | 9 | 33.68 | 343.7 | 1.40 | 19.27 | Anhydrous |
| 9 | 2 | 4.91 | 20 | 10 | 0.68 | 6.94 | 1.41 | 18.85 | Monohydrate |
| 10 | 2 | 4.91 | 20 | 10 | 0.8 | 8.16 | 1.66 | 19.00 | Monohydrate |
| 11 | 0.6 | 1.47 | 9.1 | 15 | 0.32 | 3.265 | 2.20 | 18.8 | Monohydrate |

*seeded with seed crystals of monohydrate.

The theoretical phosphate content for sitagliptin phosphate monohydrate is 18.72% and that of sitagliptin phosphate anhydrous is 19.38%. When the sitagliptin free base of Formula (II) was reacted with less than 1.4 mole equivalent of 85% phosphoric acid, the resulting sitagliptin phosphate anhydrous or monohydrate were having less phosphate content compared to the theoretical requirement. The Table-1 herein above summarizes the usage of different mole equivalent of 85% phosphoric acid against one mole equivalent of sitagliptin free base.

The sitagliptin phosphate anhydrous of Formula (I') may be obtained by removal of solvent by the known techniques in the art but not limited to distillation, distillation under vacuum, filtration, decantation, evaporation or evaporation under reduced pressure, centrifugation and the like. In particular, sitagliptin phosphate anhydrous of Formula (I') may be obtained by filtration of obtained precipitates and drying. The sitagliptin phosphate anhydrous thus obtained was anhydrous having moisture content less than 0.5% wt/wt.

Figure 1:
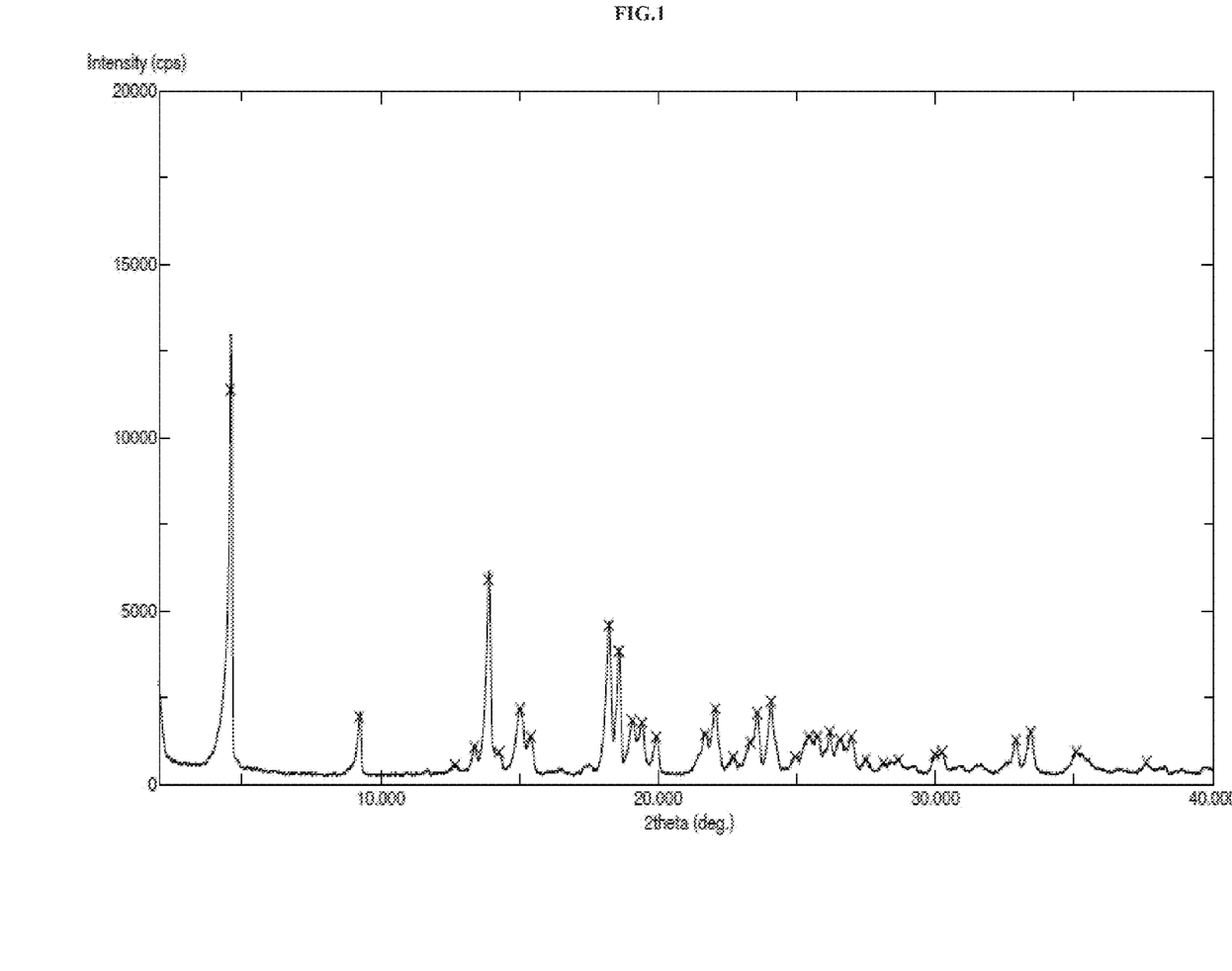
FIG. 1. Shows the X-ray diffractogram (XRD) of sitagliptin phosphate anhydrous as per example-4.
Figure 2:
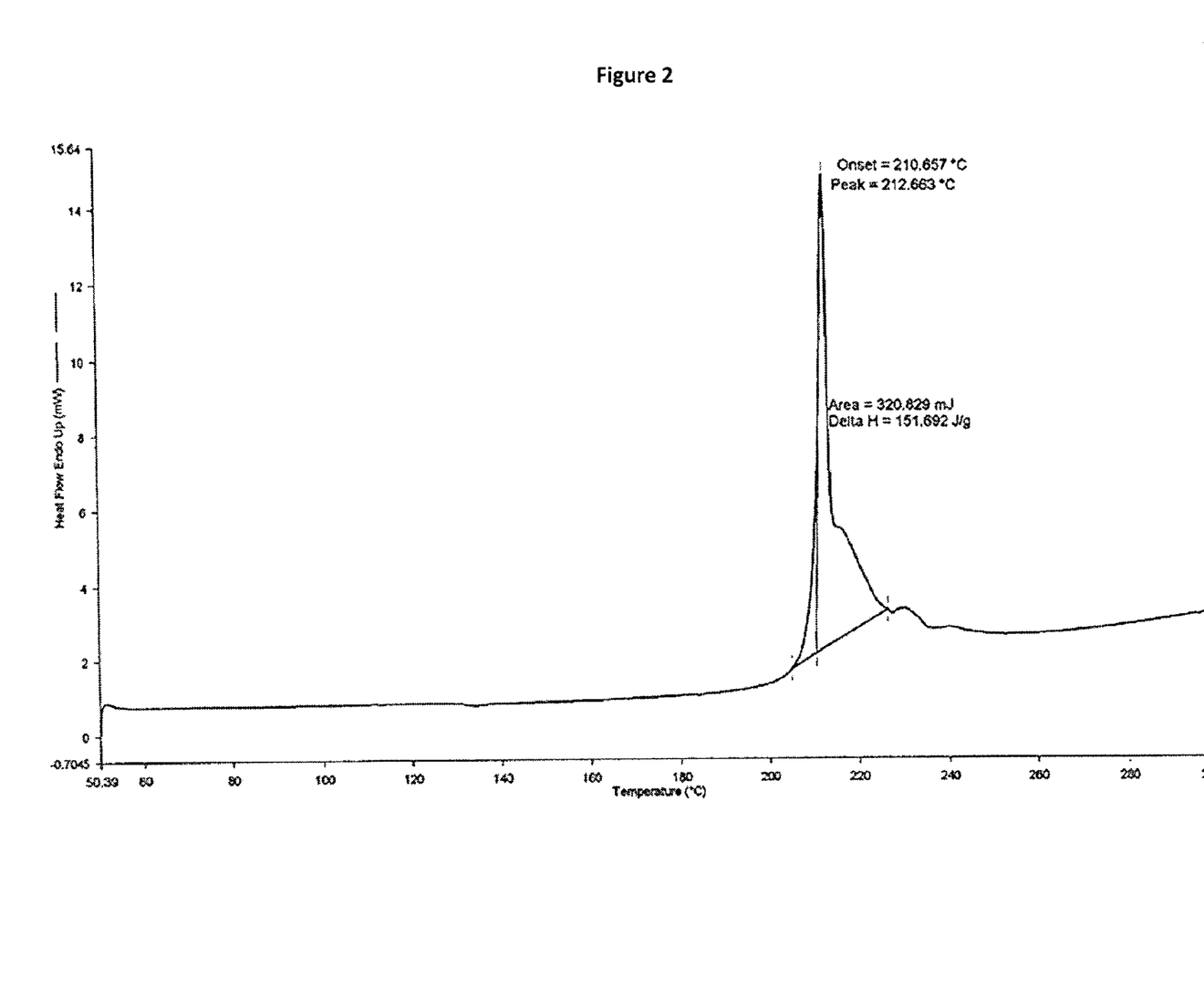
FIG. 2. Shows the differential scanning calorimetry (DSC) of sitagliptin phosphate anhydrous as per example-4.

The sitagliptin phosphate anhydrous of Formula (I') is crystalline in nature and may be characterized by X-ray powder diffraction pattern substantially as depicted in FIG. 1 and differential scanning calorimetry substantially as depicted in FIG. 2.

The sitagliptin phosphate anhydrous may be characterized by X-ray powder diffraction pattern having characteristic peaks at about 4.6°, 9.3°, 13.4°, 13.9°, 15.0°, 18.2°, 19.2°, 19.9°, 21.4°, 25.4° and 26.9°±0.2° 2θ.

The sitagliptin phosphate anhydrous of Formula (I') may be furthered characterized by differential scanning calorimetery having endothermic peak at about 212.6° C.

The sitagliptin free base of Formula (II) may be optionally converted to its monohydrate of Formula (I) by similar reaction conditions for the formation of sitagliptin phosphate anhydrous with at least 1.4 mole equivalents of phosphoric acid optionally in presence of seed crystals. In particular, the sitagliptin free base of Formula (II) may be treated with at least 1.4 mole equivalents of 85% phosphoric acid in mixture of isopropanol and water at about 75° C. to 80° C. optionally in presence of seed crystals of sitagliptin phosphate monohydrate.

In general, the seed crystals for the preparation of sitagliptin phosphate monohydrate may be prepared by process as disclosed in the prior art U.S. Pat. No. 7,326,708 B2.

Figure 3:
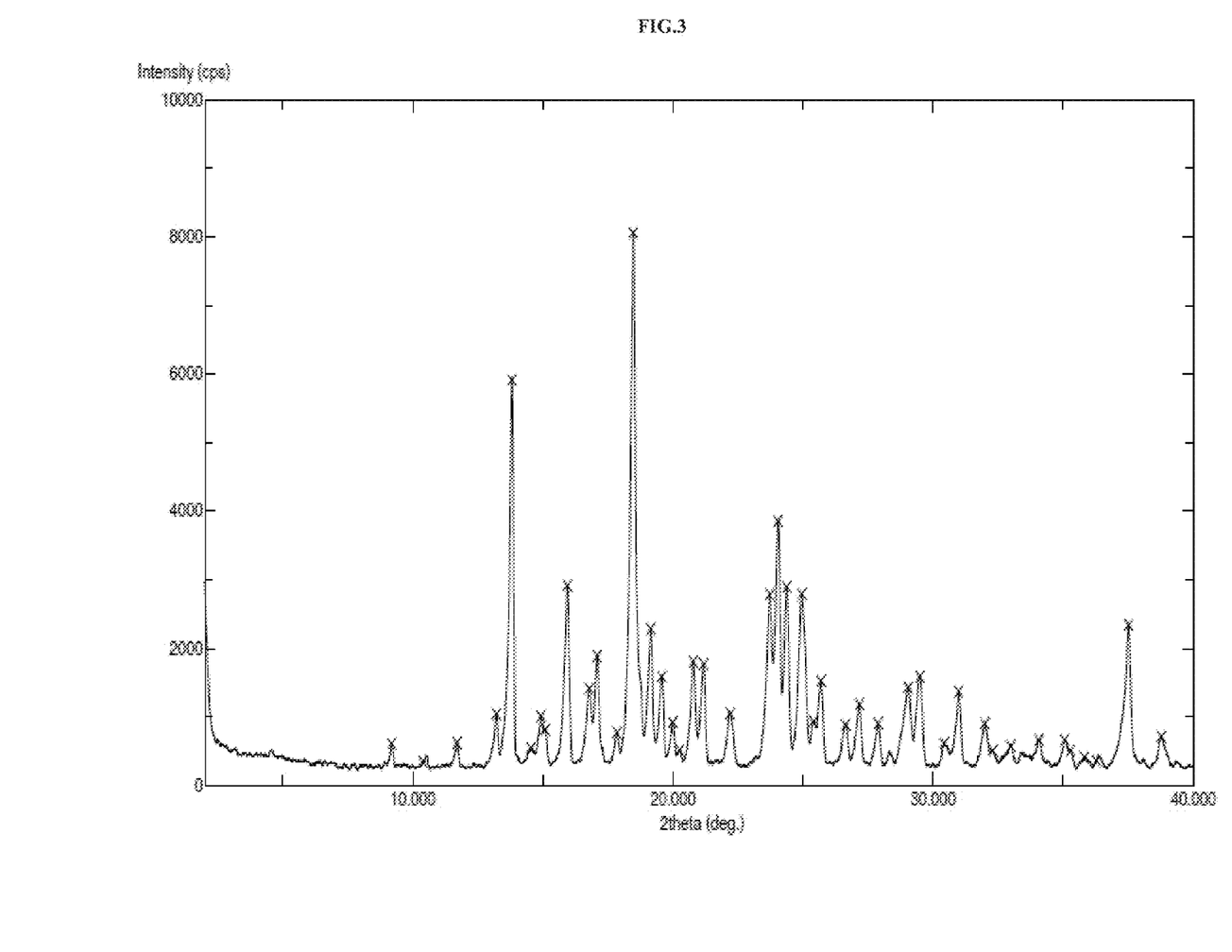
FIG. 3. Shows the X-ray diffractogram (XRD) of sitagliptin phosphate Monohydrate as per example-3.
Figure 4:
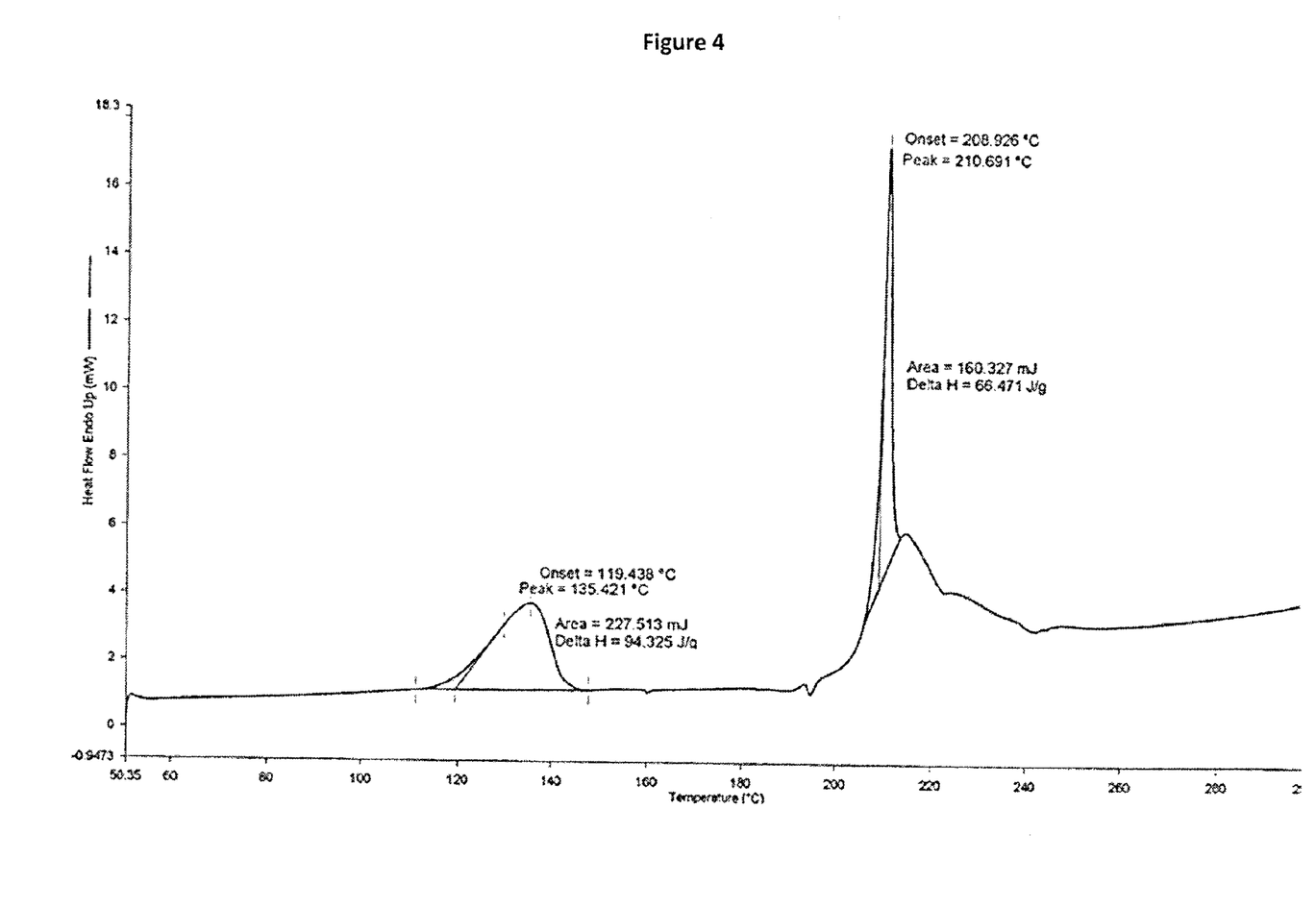
FIG. 4. Shows the differential scanning calorimetry (DSC) of sitagliptin phosphate Monohydrate as per example-3.

The sitagliptin phosphate monohydrate of Formula (I) thus obtained is crystalline in nature and may be characterized by X-ray powder diffraction pattern substantially as depicted in FIG. 3 and differential scanning calorimetry substantially as depicted in FIG. 4.

The sitagliptin phosphate monohydrate may be characterized by X-ray powder diffraction pattern having characteristic peaks at about 13.2°, 13.8°, 15.9°, 18.4°, 19.1°, 21.2°, 24.0°, 25.0°, 25.7°, 29.5°, and 30.9°±0.2° 2θ.

The sitagliptin phosphate monohydrate may be characterized by differential scanning calorimetery having endothermic peaks at about 135.4° C. and 210.6° C.

In another general aspect, there is provided an improved process for the preparation of (R)-tert-butyl 4-oxo-4-(3-(trifluoromethyl)-5,6-dihydro-[1,2,4]triazolo[4,3-a]pyrazin-7(8H)-yl)-1-(2,4,5-trifluorophenyl)butan-2-ylcarbamate of Formula (III), an intermediate for sitagliptin phosphate anhydrous of Formula (I') or monohydrate of Formula (I), the process comprising coupling (3R)—N-(tert-butoxycarbonyl)-3-amino-4-(2,4,5-trifluorophenyl)butanoic acid of Formula (V) with 3-(trifluoromethyl)-5,6,7,8-tetrahydro-1,2,4-triazolo-[4,3-a]pyrazine or its hydrochloride of Formula (IV), (VI)

in presence of coupling agent TBTU and a base in organic solvent to obtain reaction mixture and obtaining compound (III) by addition of water in the reaction mixture.

In another general aspect, there is provided sitagliptin phosphate anhydrous of Formula (I') or its monohydrate of Formula (I) prepared by the process of present invention and having purity greater than 99.90%, or greater than 99.95% when measured by area percentage of HPLC.

In another general aspect, there is provides sitagliptin phosphate anhydrous of Formula (I') or its monohydrate of Formula (I) substantially free from impurities, prepared by the process of present invention.

In another general aspect, there is provided a pharmaceutical composition comprising therapeutically effective amount of sitagliptin phosphate anhydrous of Formula (I') and one or more of pharmaceutically acceptable carriers, diluents or excipients.

In another general aspect, there is provided a pharmaceutical composition comprising therapeutically effective amount of sitagliptin phosphate monohydrate of Formula (I) and one or more of pharmaceutically acceptable carriers, diluents or excipients.

In another general aspect, sitagliptin phosphate may be prepared by the reaction scheme-1 as shown below, which is also the scope of the present invention.

Scheme-1

(I) Sitagliptin Phosphate Monohydrate (II) Sitagliptin free base

(I') Sitagliptin Phosphate Anhydrous

The present invention is further illustrated by the following example which is provided merely to be exemplary of the invention and do not limit the scope of the invention.

EXAMPLES

Example-1

Preparation of (R)-tert-butyl 4-oxo-4-(3-(trifluoromethyl)-5,6-dihydro-[1,2,4]triazolo[4,3-a]pyrazin-7 (8H)-yl)-1-(2,4,5-trifluorophenyl) butan-2-ylcarbamate of Formula (III)

(V)

(III)

In 250 mL three necked round bottom flask equipped with mechanical stirrer, thermometer and an addition funnel, were added 400 mL DMF, 100 g (3R)—N-(tert-butoxycarbonyl)-3-amino-4-(2,4,5-trifluorophenyl) butanoic acid of Formula (V) and 72 g 3-(trifluoromethyl)-5,6,7,8-tetrahydro-1,2,4-triazolo-[4,3-a]pyrazine hydrochloride of Formula (IV). The reaction mixture was cooled to 0 to 5° C. and 106 g TBTU was added. 116.3 g DIPEA was added to the reaction mixture and stirred for 1 hour. After the completion of reaction, 1 L water and 600 mL 1% NaHCO$_3$ was added. The reaction mixture was stirred for 1 hour at 25° C. to 35° C. The precipitates were filtered and washed with water. The product was dried under vacuum at 60° C. for 4 hours to obtain 151.9 g of title compound.

Example-2

Preparation of Sitagliptin Free Base of Formula (II)

In 2 L four necked round bottom flask equipped with mechanical stirrer, thermometer and an addition funnel, was added 150 g compound (III) and 450 mL of IPA. 285.8 mL IPA.HCl 16.6% solution was added to the reaction mixture and heated to 50° C. for 4 hours. After the completion of reaction, IPA was distilled completely to get a semisolid mass under vacuum at about 60° C. followed by addition of 600 mL MDC and 600 mL water. The reaction mixture was treated with 40%) sodium hydroxide solution to adjust the pH of 12 to 13. The separated aqueous layer was extracted with 300 mL MDC. The MDC layer was washed with 300 mL water, charcoalized and filtered. The filtrate was distilled completely to remove MDC at about 50° C. and treated with 150 mL of cyclohexane. The reaction mixture was distilled to remove cyclohexane and 150 mL of isopropanol and 750 mL of cyclohexane was added. The reaction mixture was heated to 70° C. to 75° C. for 1 hour and cooled to 0° C. to 5° C. The product was filtered and washed with cyclohexane and dried at 50° C. to obtain 102 g of sitagliptin free base.

Example-3

Preparation of Sitagliptin Phosphate Monohydrate (I)

In 2 L three necked round bottom flask equipped with mechanical stirrer, thermometer and an addition funnel, was added 700 mL IPA, 100 g sitagliptin free base as obtained in example 2 and 200 mL water. 33.38 g of 85% phosphoric acid was added to the reaction mixture and heated to 75 to 80° C. for 1 hour. The seed crystals of sitagliptin phosphate monohydrate (1 g) was added at temperature of 58 to 60° C. and cooled to 0 to 5° C. The reaction mixture was stirred for 1 hour at 0 to 5° C. and filtered. The solid was washed with 200 mL IPA and dried under vacuum at 50° C. for 4 hours to obtain 125 g of title compound.

M/C: 3.82% (XRD: FIG. 3) and (DSC: FIG. 4).

Example-4

Preparation of Sitagliptin Phosphate Anhydrous (I')

17
-continued (I')

In 2 L three necked round bottom flask equipped with mechanical stirrer, thermometer and an addition funnel, was added 700 mL IPA, 100 g sitagliptin free base as obtained in example 2 and 200 mL water. 33.38 g of 85% phosphoric acid was added to the reaction mixture and heated to 75 to 80° C. for 1 hour. The reaction mixture was cooled to 0 to 5° C. and stirred for 1 hour and filtered. The solid was washed with 200 mL IPA and dried under vacuum at 60° C. for 4 hours to obtain 110 g of title compound.

M/C=0.31% (XRD: FIG. 1) and (DSC: FIG. 2).

Example-5

Preparation of Sitagliptin Phosphate Anhydrous (I')

In 2 L three necked round bottom flask equipped with mechanical stirrer, thermometer and an addition funnel, was added 700 mL IPA, 100 g sitagliptin free base as obtained in example 2 and 100 mL water. 33.38 g of 85% phosphoric acid was added to the reaction mixture and heated to 75 to 80° C. for 1 hour. The reaction mixture was cooled to 0 to 5° C. and stirred for 1 hour and filtered. The solid was washed with 200 mL IPA and dried under vacuum at 60° C. for 4 hours to obtain 114 g of title compound.

Figure 5:
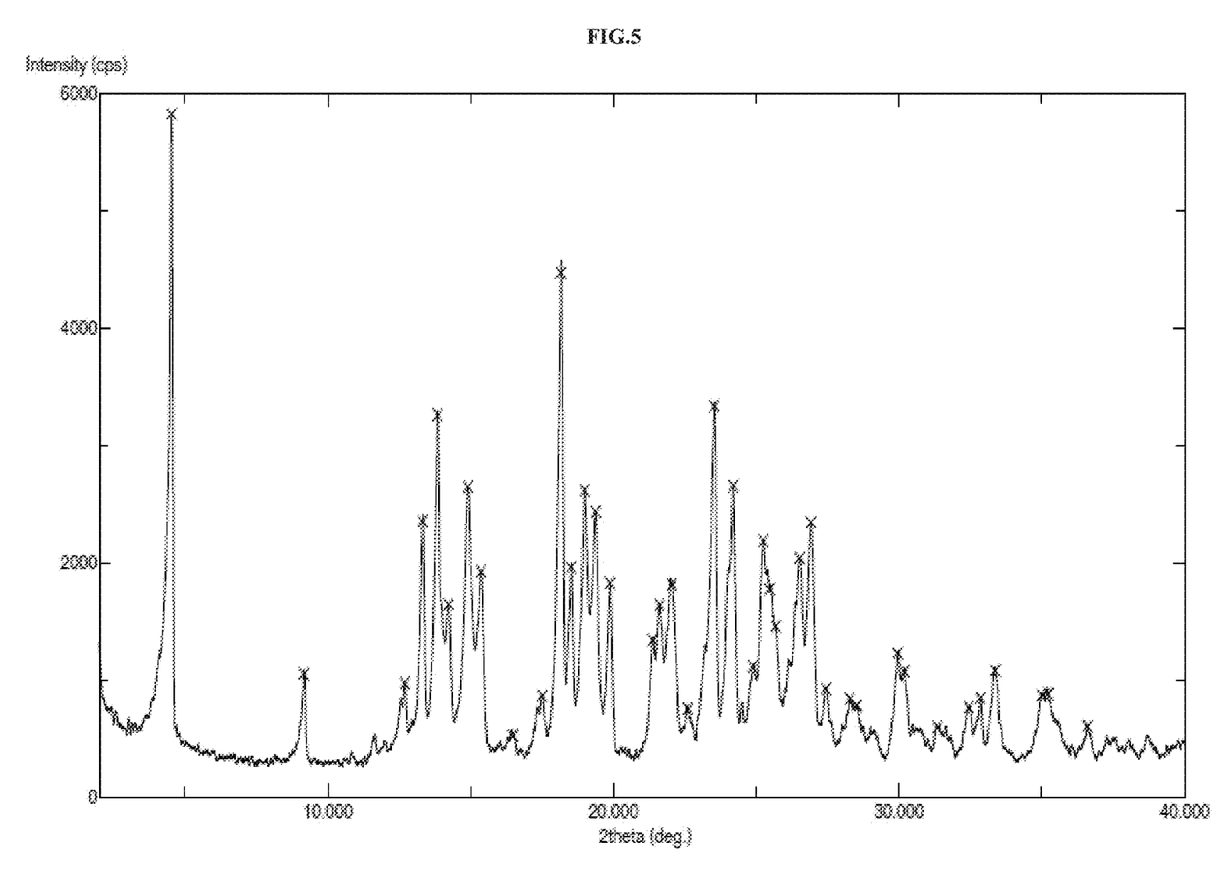
FIG. 5. Shows the X-ray diffractogram (XRD) of sitagliptin phosphate anhydrous as per example-5.

M/C=0.45% (XRD: FIG. 5)

While the present invention has been described in terms of its specific embodiments, certain modifications and equivalents will be apparent to those skilled in the art and are intended to be included within the scope of the present invention.

We claim:

1. A process for the preparation of sitagliptin phosphate anhydrous of Formula (I') or monohydrate of Formula (I), (I')

18
-continued (I)

the process comprising:
(a) coupling (3R)—N-(tert-butoxycarbonyl)-3-amino-4-(2,4,5-trifluorophenyl)butanoic acid of Formula (V), (V)

with 3-(trifluoromethyl)-5,6,7,8-tetrahydro-1,2,4-triazolo-[4,3-a]pyrazine or its hydrochloride of Formula (IV), (IV)

in the presence of a coupling agent O-benzotriazol-1-yl-1,1,3-tetramethyluronium tetrafluoroborate and a base in one or more first solvents to obtain (R)-tert-butyl 4-oxo-4-(3-(trifluoromethyl)-5,6-dihydro-[1,2,4]triazolo[4,3-a]pyrazin-7(8H)-yl)-1-(2,4,5-trifluoro phenyl)butan-2-ylcarbamate of Formula (III);

(III)

(b) deprotecting the compound of Formula (III) with an acid in one or more second solvents to obtain sitagliptin free base of Formula (II) by removal of solvent; and (c) treating the sitagliptin free base of Formula (II) with at least 1.4 mole equivalent of phosphoric acid in one or more of the second solvents and recovering sitagliptin phosphate anhydrous of Formula (I') having more than 19.0% phosphate content by ion chromatography (IC); or (d) treating the sitagliptin free base of Formula (II) with at least 1.4 mole equivalent of phosphoric acid in one or more of the second solvents optionally in the presence of seed crystals and recovering sitagliptin phosphate monohydrate of Formula (I) having more than 18.0% phosphate content by IC.

2. The process according to claim 1, wherein the base comprises one or more of alkali metal hydroxides selected from the group consisting of sodium hydroxide, potassium hydroxide, and lithium hydroxide; alkali metal carbonates selected from the group consisting of sodium carbonate and potassium carbonate; and alkali metal bicarbonates selected from the group consisting of sodium bicarbonate, potassium bicarbonate; and ammonia or its aqueous solution, or an organic base selected from the group consisting of methyl amine, ethyl amine, TEA, TBA, DIPA, DIPEA, pyridine, piperidine, morpholine, DBU, DABCO and DBN.

3. The process according to claim 1, wherein the first solvent comprises one or more of water, methanol, ethanol, isopropanol, ethyl acetate, isopropyl acetate, n-butyl acetate, acetone, methyl ethyl ketone, methyl isobutyl ketone, DMF, DMAc, DMSO, NMP, MDC, THF, and 1,4-dioxane.

4. The process according to claim 1, wherein the acid is selected from the group consisting of hydrochloric acid, triflouroacetic acid, sulfuric acid, pivalic acid, acetic acid and formic acid.

5. The process according to claim 1, wherein the second solvent comprises one or more alcohols selected from the group consisting of methanol, ethanol, n-propanol, isopropanol, and n-butanol; a ketone selected from the group consisting of acetone, methyl ethyl ketone and methyl isobutyl ketone; a chloro solvents selected from the group consisting of MDC, chloroform, ethylene dichloride and chlorobenzene; a hydrocarbons selected from the group consisting of toluene, xylene, and ethylbenzene; an ester selected from the group consisting of ethyl acetate, isopropyl acetate, and n-butyl acetate; an ether selected from the group consisting of tetrahydrofuran, diethyl ether, diisopropyl ether, and methyl tert-butyl ether or a polar solvents selected from the group consisting of water, DMF, DMAc, DMSO, and NMP.

6. The process according to claim 1, wherein the sitagliptin free base of Formula (II) is obtained by a process comprising:
(a) removal of the first solvent to obtain sitagliptin free base as a semi-solid mass;
(b) treating the semi-solid mass with a mixture of water immiscible solvent and water;
(c) treating the reaction mixture with a base to adjust the pH to 12-13;
(d) removing the separated aqueous layer and concentrating the organic layer to obtain a semi-solid mass; and
(e) treating the semi-solid mass with one or more solvents to obtain the sitagliptin free base of Formula (II).

7. The process according to claim 6, wherein the water immiscible solvent comprises one or more of methylene dichloride, toluene, xylene, and ethyl acetate.

8. The process according to claim 6, wherein the base comprises one or more alkali metal hydroxides selected from the group consisting of sodium hydroxide, potassium hydroxide, and lithium hydroxide; an alkali metal carbonates selected from the group consisting of sodium carbonate, and potassium carbonate an alkali metal bicarbonate selected from the group consisting of sodium bicarbonate and potassium bicarbonate; or ammonia or its aqueous solution.

9. The process according to claim 6, wherein the one or more solvents in step (e) comprises one more alcohols selected from the group consisting of methanol, ethanol, n-propanol, isopropanol, and n-butanol; a ketone selected from the group consisting of acetone, methyl ethyl ketone, and methyl isobutyl ketone; a hydrocarbon selected from the group consisting of toluene, xylene, ethylbenzene, hexane, heptane, and cyclohexane; an ester selected from the group consisting of ethyl acetate, isopropyl acetate; and n-butyl acetate; or an ether selected from the group consisting of tetrahydrofuran, diethyl ether, diisopropyl ether and methyl tert-butyl ether or a mixture thereof.

10. The process according to claim 1, comprising the step (c) of treating the sitagliptin free base of Formula (II) with at least 1.4 mole equivalent of phosphoric acid in one or more of the second solvents and recovering sitagliptin phosphate anhydrous of Formula (I') having a phosphate content of at least 19.27%.

11. The process according to claim 1, comprising the step (d) of treating the sitagliptin free base of Formula (II) with at least 1.4 mole equivalent of phosphoric acid in one or more of the second solvents optionally in the presence of seed crystals and recovering sitagliptin phosphate monohydrate of Formula (I) having a phosphate content of at least 18.02%.

12. A process for the preparation of sitagliptin phosphate anhydrous of Formula (I') or monohydrate of Formula (I), the process comprising:

(a) treating sitagliptin free base with at least 1.4 mole equivalent of phosphoric acid in one or more solvents and recovering sitagliptin phosphate anhydrous of Formula (I') having more than 19.0% phosphate content by ion chromatography (IC); or

(b) treating sitagliptin free base with at least 1.4 mole equivalent of phosphoric acid in one or more solvents optionally in the presence of seed crystals and recovering sitagliptin phosphate monohydrate of Formula (I) having more than 18.0% phosphate content by IC.

13. The process according to claim 12, wherein the one or more solvents comprising an alcohol selected from the group consisting of methanol, ethanol, isopropanol and butanol; or a mixture thereof with water.

14. The process according to claim 12, comprising the step (a) of treating the sitagliptin free base with at least 1.4 mole equivalent of phosphoric acid in one or more of the solvents and recovering sitagliptin phosphate anhydrous of Formula (I') having a phosphate content of at least 19.27%.

15. The process according to claim 12, comprising the step (b) of treating the sitagliptin free base with at least 1.4 mole equivalent of phosphoric acid in one or more of the solvents optionally in the presence of seed crystals and recovering sitagliptin phosphate monohydrate of Formula (I) having a phosphate content of at least 18.02%.

16. A process for the preparation of (R)-tert-butyl 4-oxo-4-(3-(trifluoromethyl)-5,6-dihydro-[1,2,4]triazolo[4,3-a]pyrazin-7(8H)-yl)-1-(2,4,5-trifluoro-phenyl)butan-2-ylcarbamate of Formula (III), an intermediate for sitagliptin phosphate anhydrous of Formula (I') or monohydrate of Formula (I), (III)

the process comprising coupling (3R)—N-(tert-butoxycarbonyl)-3-amino-4-(2,4,5-trifluoro-phenyl)butanoic acid of Formula (V) with 3-(trifluoromethyl)-5,6,7,8-tetrahydro-1,2,4-triazolo-[4,3-a]pyrazine or its hydrochloride of Formula (IV),

(V)

(IV)

in the presence of a coupling agent O-benzotriazol-1-yl-1,1,3-tetramethyluronium tetrafluoroborate and a base in one or more solvents to obtain a reaction mixture and obtaining the compound (III) by the addition of water in the reaction mixture.

17. A process for the preparation of sitagliptin phosphate anhydrous of Formula (I') or monohydrate of Formula (I), (I')

(I)

comprising coupling (3R)—N-(tert-butoxycarbonyl)-3-amino-4-(2,4,5-trifluorophenyl)-butanoic acid of Formula (V) with 3-(trifluoromethyl)-5,6,7,8-tetrahydro-1,2,4-triazolo-[4,3-a]pyrazine or its hydrochloride of Formula (IV), (V)

(IV)

-continued (A)

in the presence of a coupling agent O-benzotriazol-1-yl-1,1,3-tetramethyluronium tetrafluoroborate of Formula (A) to obtain (R)-tert-butyl 4-oxo-4-(3-(trifluoromethyl)-5,6-dihydro-[1,2,4]triazolo[4,3-a]pyrazin-7(8H)-yl)-1-(2,4,5-trifluorophenyl)butan-2-yl carbamate of Formula (III) and converting (R)-tert-butyl 4-oxo-4-(3-(trifluoromethyl)-5,6-dihydro-[1,2,4]triazolo[4,3-a]pyrazin-7(8H)-yl)-1-(2,4,5-trifluorophenyl)butan-2-yl carbamate of Formula (III) to sitagliptin phosphate anhydrous of Formula (I') or monohydrate of Formula (I).

* * * * *